United States Patent [19]

Gentile et al.

[11] Patent Number: 5,294,544
[45] Date of Patent: Mar. 15, 1994

[54] BIOLOGICALLY ACTIVE FACTOR

[75] Inventors: Patrick S. Gentile, Louisville, Ky.; Charlie R. Mantel, Plainfield; Hal E. Broxmeyer, Indianapolis, both of Ind.

[73] Assignee: Research Corporation Technologies, Inc., Tucson, Ariz.

[21] Appl. No.: 887,681

[22] Filed: May 22, 1992

Related U.S. Application Data

[62] Division of Ser. No. 436,164, Nov. 13, 1989, Pat. No. 5,149,544.

[51] Int. Cl.⁵ .......................... C12P 21/00; C12N 5/06
[52] U.S. Cl. .................................. 435/70.4; 435/70.1; 435/7.3; 435/240.2; 435/240.1; 435/240.3; 514/2; 530/300; 424/520; 424/529; 424/579; 424/577
[58] Field of Search ................... 435/70.1, 70.3, 240.1, 435/240.2, 240.3; 514/2, 12, 21; 530/300, 380, 412, 416, 414, 418; 424/520, 529, 577, 579

[56] References Cited

U.S. PATENT DOCUMENTS

| 4,064,007 | 12/1977 | Choay et al. | 424/115 |
| 4,384,991 | 5/1983 | Balazs et al. | 530/300 |
| 4,438,032 | 3/1984 | Golde et al. | 435/172.2 |
| 4,546,082 | 10/1985 | Kurjan et al. | 435/172.3 |
| 4,588,684 | 5/1986 | Brake | 435/69.4 |
| 4,775,622 | 10/1988 | Hitzeman et al. | 435/69.4 |

FOREIGN PATENT DOCUMENTS 162812 11/1985 European Pat. Off. .
263072 4/1988 European Pat. Off. .

OTHER PUBLICATIONS

Bagby et al., *J. Clin. Invest.*, 68, 56–63 (1981).
Bagby et al., *J. Clin. Invest.*, 71, 340–44 (1983).
Broxmeyer et al., *Blood*, 55, 324–33 (1980).
Broxmeyer et al., *Blood*, 60, 595–607 (1982).
Broxmeyer et al., *Blood*, 73, 74–79 (1989).
Broxmeyer et al., *Blood Cells*, 10, 397–426 (1984).
Broxmeyer, *Blood Cells*, 13, 31–48 (1987).
Broxmeyer, *Int. J. Cell Cloning*, 4, 378–405 (1986).
Broxmeyer et al., *J. Clin. Invest.*, 79, 721–730 (1987).
Broxmeyer et al., *J. Exp. Med.*, 148, 1052–1067 (1978).
Broxmeyer et al., *J. Exp. Med.*, 153, 1426–1444 (1981).
Broxmeyer and Platzer, *J. Immunol.*, 133, 306–314 (1984).
Broxmeyer and Williams, *CRC Crit. Rev. Oncol.-/Hematol.* 8, 173–226 (1988).
Fletcher and Willars, *Blood Cells*, 11, 447–54 (1986).
Frindel and Guigon, *Exp. Hemat.*, 5, 74–76 (1977).
Genitle and Broxmeyer, *Blood*, 61, 982–93 (1983).
Genitle and Pelus, *Exp. Hematol.*, 15, 119–126 (1987).
Gentile and Pelus, *The Journal of Immunology*, 141, 2714–20 (1988).
Gentile et al., *Blood*, 62, 1100–1107 (1983).
Laemmli, *Nature*, 227, 680–685 (1970).
Levi et al., *Gene*, 51, 267 (1987).
Metcalf and Johnson, *J. Cell Physiol.*, 96, 31 (1978).
Naldini et al., *The Journal of Immunology*, 139, 1880 (1987).
Pelus and Gentile, *Blood*, 71, 1633–40 (1988).
Pelus et al., *Cell Tissue Kinet.*, 14, 515–26 (1981).
Pelus et al., *J. Exp. Med.*, 150, 277–92 (1979).
Rogers et al., *Cellular Immunology*, 50, 82–93 (1980).
Taniguchi et al., *Blood*, 73, 907–913 (1989).
Wright and Lorimore, *Cell Tissue Kinet.*, 20, 191–203 (1987).
Zucali et al., *Blood*, 74, 1531–1536 (1989).
Broxmeyer, et al., *J. Exp. Med.*, 170, 1583–1594 (1989).
Broxmeyer, et al., *Blood*, 76, 1110–1116 (1990).
Broxmeyer, et al., *J. Immunol.*, 147, 2586–2594 (1991).
Szmitkowski et al., *Experientia*, 37, 1202 (1981).

*Primary Examiner*—Christopher S. F. Low
*Attorney, Agent, or Firm*—Willian Brinks Hofer Gilson & Lione

[57] ABSTRACT

The invention comprises a factor having the following characteristics:
  a) It inhibits granulocyte-macrophage colony and cluster formation;
  b) It has a molecular weight of about 8 kDa as determined by SDS-PAGE;
  c) It has a weak anionic charge at pH 7.4 as shown by anion exchange chromatography;
  d) It has a flattened isoelectric titration curve as shown by anion exchange chromatography; and
  d) It is a protein.

The invention also comprises methods of making and using the factor and compositions comprising the factor.

6 Claims, 7 Drawing Sheets

BIOLOGICALLY ACTIVE FACTOR

This is a division, of application Ser. No. 07/436,164, filed Nov. 13. 1989 now U.S. Pat. No. 5,149,544.

BACKGROUND OF THE INVENTION

This invention relates to biologically active factors. In particular, the invention relates to inhibitors of hematopoietic progenitor cell proliferation and differentiation.

There are several known stimulators and inhibitors of hematopoietic progenitor cell proliferation and differentiation. For instance, regulatory molecules termed colony-stimulating factors (CSF) stimulate clonal macrophage and/or granulocyte expansion and differentiation from committed hematopoietic progenitor cells. Broxmeyer, *Int. J. Cell Cloning*, 4, 378–405 (1986); Broxmeyer and Williams, *CRC Crit. Rev. Oncol.-/Hematol.*, 8, 173–226 (1988). Other substances are known which inhibit hematopoietic progenitor cell proliferation and differentiation.

One such inhibitor is lactoferrin (LF). In vitro. LF is reported to inhibit the production by mononuclear cells of CSF's which stimulate granulocyte and macrophage colony formation. Broxmeyer et al., *J. Exp. Med.*, 148, 1052–1067 (1978); Pelus et al., *J. Exp. Med.*, 150, 277–92 (1979); Broxmeyer et al., *Blood*, 55, 324–33 (1980); Bagby et al., *J. Clin. Invest.*, 68, 56–63 (1981); Pelus et al., *Cell Tissue Kinet.*, 14, 515–26 (1981); Broxmeyer and Platzer, *J. Immunol.*, 133, 306–314 (1984); Fletcher and Willars, *Blood Cells*, 11, 447–54 (1986). LF may act directly on the monocytes to inhibit production of CSF's, but evidence has also been presented that LF inhibits the production of CSF by suppressing the production by monocytes of a monokine (e.g., interleukin-1) that recruits other cells (such as skin-derived human fibroblasts) to produce CSF. Bagby et al., *J. Clin. Invest.*, 71, 340–44 (1983); Zucali et al., *Blood*, 74, 1531–36 (1989). See also. Broxmeyer et al., *Blood Cells*, 13, 31–48 (1987).

In vivo, iron-saturated human LF decreases the cycling status and the absolute numbers of murine marrow and spleen granulocyte-macrophage (CFU-GM), erythroid (BFU-E) and multipotential (CFU-GEMM) progenitor cells, whereas heat-inactivated LF does not. Gentile and Broxmeyer, *Blood*, 61, 982–93 (1983); Broxmeyer et al., *Blood Cells*, 13, 31–48 (1987). It is believed that the myelosuppressive effects of LF in vivo may result indirectly from the decreased release of growth factors. Broxmeyer et al., *Blood Cells*, 13, 31–48 (1987); Broxmeyer et al., *J. Clin. Invest.*, 79, 721–30 (1987).

Acidic isoferritin (AIF) has been reported to inhibit colony formation by CFU-GM, BFU-E and CFU-GEMM progenitor cells. Broxmeyer et al., *J. Exp. Med.*, 153, 1426–44 (1981); Broxmeyer et al., *Blood*, 60, 595 (1982); Broxmeyer et al., *Blood Cells*, 10, 397–426 (1984). In mice, human AIF suppresses the numbers of CFU-GM, BFU-E and CFU-GEMM per femur, decreases the cycling status of these cells and decreases the number of nucleated cells in the bone marrow and peripheral blood. Broxmeyer et al., *Blood Cells*, 10, 397–426 (1984); Broxmeyer et al., *Blood*, 73, 74–79 (1989). There is evidence that the inhibitory activity resides in a subpopulation of AIF molecules. Broxmeyer et al., *Blood Cells*, 10, 397–426 (1984). Some cell lines producing AIF are also reported to produce other unidentified inhibitory activities. Broxmeyer et al., *Blood*, 60, 595–607 (1982).

In vitro, prostaglandin E (PGE) inhibits the proliferation of CFU-GM, selectively inhibits CFU-GM in S-phase of the cell cycle and demonstrates a preferential inhibitory effect on monocytopoiesis. Pelus et al., *J. Exp. Med.*, 150, 277–92 (1979); Pelus et al., *Cell Tissue Kinet.*, 14, 515–26 (1981); Pelus and Gentile, *Blood*, 71, 1633–40 (1988). Intravenous administration of prostaglandin $E_2$ ($PGE_2$) to rebounding or normal mice results in significant inhibition of total nucleated cellularity and absolute number of CFU-GM in spleen and bone marrow, preferential inhibition of monocyte production, and selective inhibition of CFU-GM in S-phase of the cell cycle. Gentile et al., *Blood*, 62, 1100–1107 (1983); Gentile and Pelus, *Exp. Hematol.*, 15, 119–256 (1987); Pelus and Gentile, *Blood*, 71, 1633–40 (1988).

Pelus and Gentile, *Blood*, 71, 1633–40 (1988) reports that the intravenous injection of $PGE_2$ into intact mice induces a suppressor mechanism capable of suppressing CFU-GM Inhibition of CFU-GM proliferation was observed using either bone marrow or spleen cells from such mice or by using conditioned medium (CM) prepared by culturing the bone marrow or spleen cells. The article further teaches that the CM suppresses BFU-E, as well as CFU-GM, indicating that the inhibitory activity is not restricted to granulopoiesis. The molecular weight of the inhibitory activity was estimated to be about 4–6,000.

Gentile and Pelus, *The Journal of Immunology*, 141, 2714–20 (1988) further describes this inhibitory activity found in CM prepared by culturing cells from mice that have been injected with $PGE_2$. The article teaches that morphological analysis of CFU-GM revealed an equivalent inhibition of monocyte, monocyteneutrophil and neutrophil CFU-GM in contrast to the preferential effect of $PGE_2$ on monocytopoiesis. The inhibitory activity found in the CM was lost when the CM was treated with heat (56° C. for 30 minutes or 100° C. for 5 minutes), trypsin, chymotrypsin, pronase, and neuraminidase, but not when treated with lipase. The article reports that acrylamide-agarose gel filtration of the bone marrow CM revealed an active inhibitory fraction in the range of 5.5 to 8.0 kDa.

Taniguchi et al., *Blood*, 73, 907–913 (1989) reports that CM prepared by culturing cells taken from patients suffering from hairy cell leukemia inhibits the growth of granulocyte and erythrocyte colony forming cells. However, the hairy cell CM did not inhibit colony formation by all CSF's that stimulate granulopoiesis, and the erythrocyte precursors were also heterogeneous in their response to it. The article reports that the inhibitory activity in the CM is nondialyzable, fairly stable to heat treatment and destroyed by treatment with trypsin. The CM was fractionated, and activity against granulopoiesis was found in fractions having molecular weights in the range of 4,000–8,000 and over 160,000. Using another fractionation method, the inhibitory activity against granulopoiesis was found in only one peak of 5,000–6,000 daltons. The characteristics of the inhibitory activity in the hairy cell CM were compared to those of other inhibitors of hematopoiesis in the Discussion section of the Taniguchi et al. article.

U.S. Pat. No. 4,384,991 describes an inhibitor of the proliferation of normal and leukemic myeloid cells. The inhibitor is purified from an extract of white blood cells (granulocytes) isolated from blood or from an extract of an animal organ containing granulocytes. The patent reports that the inhibitor is a polypeptide and that its amino acid composition is $Tau_1$, $Asx_1$, $Ser_2$, $Thr_1$, $Glx_3$, $Gly_2$, $Ala_1$ $(PO_4)^{2-}$. From this amino acid composition, the molecular weight can be calculated to be about 1360. The patent further reports that the inhibitor's point of attack is the $G_1$ phase of the cell cycle and that the inhibitor is thermostable.

Yet another inhibitor is described in Frindel and Guigon, *Exp. Hemat.*, 5, 74–76 (1977). The inhibitor is a cell-free extract of fetal calf bone marrow. The article reports that the extract inhibits the proliferation of bone marrow colony forming cells in irradiated mice and that the inhibitor may have a rather low molecular weight since it is dialyzable.

Wright and Lorimore, *Cell Tissue Kinet.*, 20, 191–203 (1987) teaches that medium conditioned by normal murine bone marrow cells contains an inhibitor of hematopoietic spleen colony-forming cell proliferation. The inhibitory activity can be concentrated in a nominal 50–100,000 molecular weight fraction.

Finally, Rogers et al., *Cellular Immunology*, 50, 82–93 (1980) describes a factor capable of nonspecifically suppressing phytohemagglutinin lipopolysaccharide and phytohemagglutinin lipopolysaccharide-induced mitogenesis. The factor was prepared by culturing glass-adherent T cells in the presence of $PGE_2$. The article teaches that the culture supernatants contain at least two suppressors with approximate molecular weights of 35,000 and 5,000. The inhibitory activity was resistant to boiling and treatment with RNase and DNase, but was sensitive to treatment with proteases.

SUMMARY OF THE INVENTION

A biologically active factor has been discovered which inhibits hematopoietic progenitor cell proliferation and differentiation. In particular, the factor has the following characteristics:

a) It inhibits granulocyte-macrophage colony and cluster formation;

b) It has a molecular weight of about 8 kDa as determined by sodium dodecyl sulfate polyacrylamide gel electrophoresis (SDS-PAGE);

c) It has a weak anionic charge at pH 7.4 as shown by anion exchange chromatography;

d) It has a flattened isoelectric titration curve as shown by anion exchange chromatography; and e) It is a protein.

The invention also comprises methods of making the factor. One such method comprises injecting a mouse with lactoferrin (LF) or acidic isoferritin (AIF), preferably recombinant H subunit acidic ferritin (rHF), and conditioning medium with bone marrow (BM) or spleen cells removed from the mouse.

The conditioned medium (CM) may be used as such or the factor in the CM may be purified using various purification schemes. One such method comprises subjecting the CM to size-exclusion chromatography, anion exchange chromatography, and SDS-PAGE The factor may also be prepared using recombinant DNA techniques, and the invention provides vectors comprising DNA sequences coding for the factor. Also included in the invention are hosts transformed with these vectors, and a method of producing the factor comprising culturing the transformed host in a suitable culture medium.

The invention further comprises a composition for inhibiting hematopoietic progenitor cell proliferation and differentiation comprising the factor and a physiologically acceptable carrier. Also a part of the invention is a method of inhibiting hematopoietic progenitor cell proliferation and differentiation comprising contacting the hematopoietic progenitor cells with the factor or with CM prepared as described above.

The factor can be used to study the regulation of hematopoietic cell growth and differentiation. The factor is also expected to be useful as a myeloprotective agent during irradiation therapy or chemotherapy and to be of value in treating various hematologic disorders, including leukemia.

DETAILED DESCRIPTION OF THE PRESENTLY PREFERRED EMBODIMENTS

Figure 1:
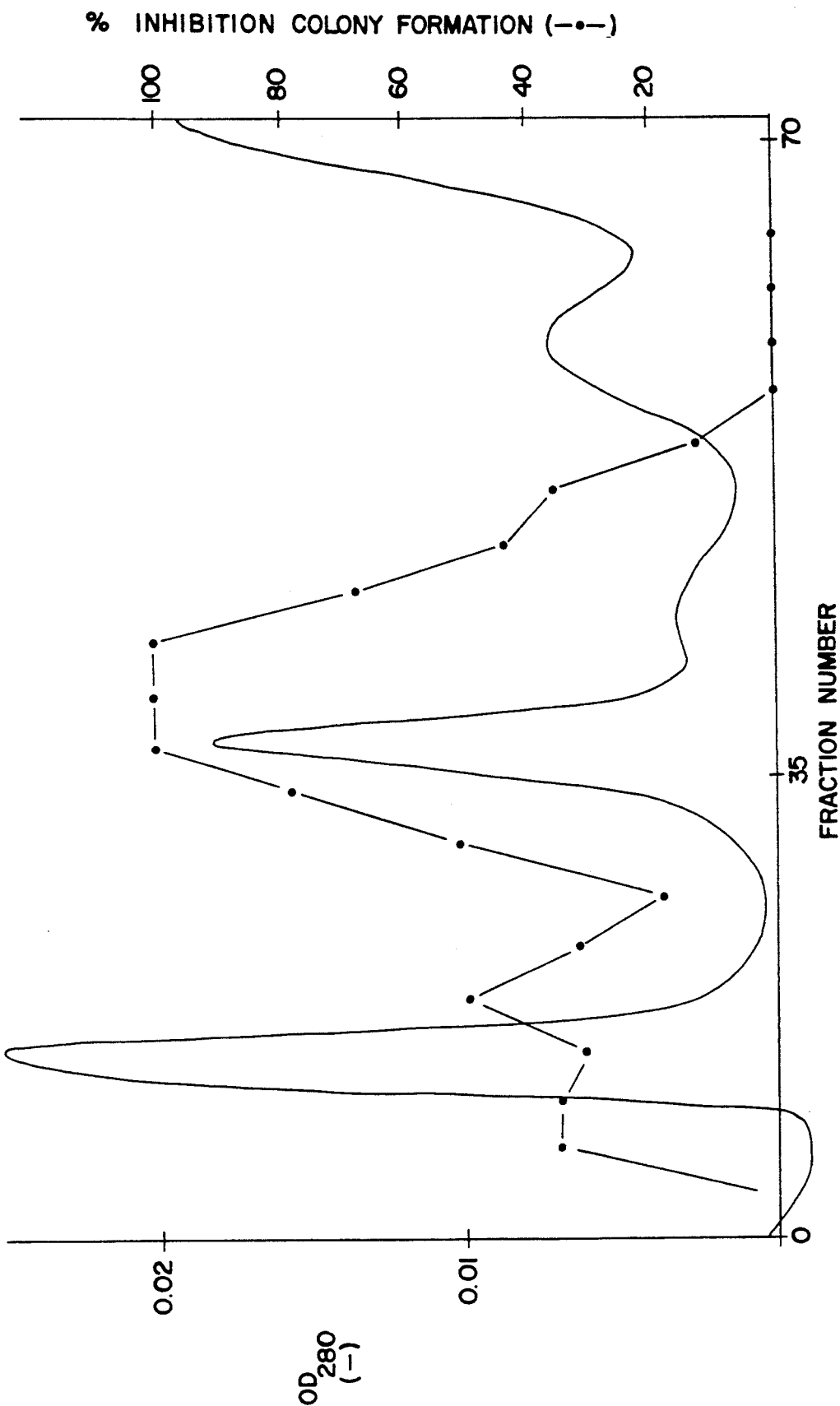
FIG. 1 shows the elution pattern from a Sephadex G25 Superfine column of concentrated CM prepared by culturing BM cells from mice injected with LF.

The factor of the invention inhibits granulocyte-macrophage colony and cluster formation. This activity can be evaluated by any standard assay for CFU-GM colony and cluster formation. Such assays and the reagents used in them are well-known. Some of these assays are described in the references discussed in the Background section. Also, one such assay is described in Example 1. Typically, the assay is performed as follows. Bone marrow or spleen cells are stimulated with CSF in an in vitro culture system. The inhibitory activity of a substance is measured as the amount that it decreases CSF-stimulated colony and cluster formation.

The factor of the invention may be induced by injecting mice with LF or AIF (preferably rHF). The injection may be intravenous or intraperitoneal.

LF is available commercially, but must be iron-saturated before use to induce production of the factor. Procedures for iron-saturating LF are known, and one such procedure is described in Example 1. Also, the iron-saturated LF must be depleted of endotoxin before use. Methods of depleting endotoxin are known; one such procedure is described in Example 1.

Ferritin is a large molecule in the molecular weight range of 550,000 which can be separated into isoforms, and the isoferritins are composed of two types of subunits (H and L) differing in charge and size. The acidic isoferritins are composed mainly of H subunits. They may be isolated from tissues containing them by known procedures, such as the procedures described in *J. Exp. Med.*, 153, 1426 (1981).

Of the forms of AIF useful for inducing production of the factor, rHF is preferred. Human rHF may be prepared as described below in Example 4.

A period of time (preferably 6 hours) after the injection of the LF or AIF, BM or spleen cells are removed from the mice and allowed to condition medium, preferably for a period of 24 to 48 hours. Methods of conditioning medium and appropriate conditions and reagents for use in such procedures are well-known to those skilled in the art. Suitable techniques are described in several of the references discussed in the Background section. Briefly, single-cell suspensions are made, and the cells are incubated in an appropriate medium under suitable culture conditions until an appreciable amount of the desired factor is present in the medium.

Preliminary data suggest that the factor may also be prepared by contacting mouse or human bone marrow and peripheral blood cells in in vitro culture with LF or rHF to produce the CM. Preliminary data further suggest that the factor is produced by adherent cells, rather than non-adherent cells, in these cell populations.

The CM containing the factor may be used as such, or the factor may be purified Appropriate purification schemes can be devised using known techniques which allow separation of the factor from other materials in the CM based on the properties of the factor.

Example 3 describes one such purification scheme. Briefly, CM prepared by culturing BM cells from mice injected with LF was concentrated by precipitation with 80% ammonium sulfate and ultrafiltration. The retentate from the ultrafiltration was subjected to size-exclusion chromatography by passing it over a Sephadex G-25 Superfine column. Fractions containing inhibitory activity were then concentrated and subjected to anion exchange chromatography on a Mono Q column at pH 7.4. The factor was only slightly retarded on the Mono Q column, indicating that it has a weak anionic charge at pH 7.4. The factor also showed essentially the same elution pattern on a Mono Q column run at pH 9.0, indicating that the factor has a flattened isoelectric titration curve.

Active fractions from the anion exchange chromatography were pooled, concentrated by ultrafiltration and then subjected to non-reducing SDS-PAGE. SDS-PAGE gels stained with silver stain showed only a single band in the lane in which the pool of active fractions was electrophoresed. Standards were also run on the gels. Using these standards, a molecular weight of approximately 8 kDa was calculated for the single band. The material eluted from the band in a non-stained gel inhibited CFU-GM colony and cluster formation. Inhibitory activity was not eluted from any other portion of the gel. The fact that the factor stained with the silver stain indicates that it is a protein or a substituted protein, such as a glycoprotein.

Similar results were obtained when CM prepared by culturing BM cells from mice injected with rHF was purified in this manner (see Example 5). In particular, only a single band having a molecular weight of about 8 kDa was observed after SDS-PAGE.

Thus, the properties of the factor may be summarized as follows:

1. It inhibits granulocyte-macrophage colony and cluster formation;
2. SDS-PAGE results indicate that the molecular weight of the factor is about 8 kDa;
3. Staining with silver stain after SDS-PAGE shows that it is a protein or a substituted protein such as a glycoprotein;
4. Its behavior during anion exchange chromatography indicates that it has a weak anionic charge at pH 7.4; and
5. Its behavior during anion exchange chromatography indicates that it has a flattened isoelectric titration curve.

Knowing these properties of the factor, other purification schemes may be devised. For instance, the factor may be purified by subjecting concentrated CM to two-dimensional electrophoresis, using isoelectric focusing in one direction and SDS-PAGE in the other direction.

Efforts are now underway to determine the amino acid sequence of the factor. Once the amino acid sequence is known, the factor may be produced by recombinant DNA techniques. Such techniques are conventional and well-known to those skilled in the art.

In particular, using the amino acid sequence, hybridization probes can be constructed that allow for the identification and isolation of complementary (c) DNA or genomic (g) DNA coding for the factor. Once isolated, the cDNA or gDNA may be inserted into a vector capable of expressing the factor in an appropriate host.

Vectors according to the invention will comprise a DNA sequence coding for the factor operatively linked to appropriate expression control sequences. Methods of effecting this operative linking, either before or after the DNA sequence is inserted into the vector, are well known. Expression control sequences include promoters, activators, enhancers, operators, ribosomal binding sites, start signals, stop signals, cap signals, polyadenylation signals, and other signals involved with the control of transcription or translation.

The vector must contain a promoter and a transcription termination signal, both operatively linked to the DNA sequence that codes for the factor. The promoter may be any DNA sequence that shows transcriptional activity in the host cell and may be derived from genes encoding homologous or heterologous proteins (preferably homologous) and either extracellular or intracellular proteins, such as amylases, glycoamylases, proteases, lipases, cellulases and glycolytic enzymes.

The promoter may be preceded by upstream activator and enhancer sequences. An operator sequence may also be included downstream of the promoter, if desired.

The vector should also have a translation start signal immediately preceding the DNA sequence coding for the factor, if the DNA sequence does not itself begin with such a start signal. There should be no stop signal between the start signal and the end of the DNA sequence coding for the factor.

Expression control sequences suitable for use in the invention are well known. They include those of the *E. coli lac* system, the *E. coli trp* system, the TAC system and the TRC system; the major operator and promoter regions of bacteriophage lambda; the control region of filamentaceous single-stranded DNA phages; the expression control sequences of other bacteria; promoters derived from genes coding for *Saccharomyces cerevisiae* TPI, ADH, PGK and alpha-factor; promoters derived from genes coding for *Aspergillus oryzae* TAKA amylase and *A. niger* glycoamylase, neutral alpha-amylase and acid stable alpha-amylase; promoters derived from genes coding for *Rhizomucor miehei* aspartic proteinase and lipase; and other sequences known to control the expression of genes of prokaryotic cells, eukaryotic cells, their viruses, or combinations thereof.

The vector must also contain one or more replication systems which allow it to replicate in the host cells. In particular, when the host is a yeast, the vector should contain the yeast 2 u replication genes REP-1-3 and origin or replication.

The vector should further include one or more restriction enzyme sites for inserting DNA sequences into the vector, and a DNA sequence coding for a selectable or identifiable phenotypic trait which is manifested when the vector is present in the host cell ("a selection marker").

Suitable vectors for use in the invention are well known. They include pUC (such as pUC8 and pUC4K), pBR (such as pBR322 and pBR328), pUR (such as pUR288), phage λ and YEp (such as YEp24) plasmids and derivatives thereof.

In a preferred embodiment, a DNA sequence encoding a signal or signal-leader sequence, or a functional fragment thereof, is included in the recombinant DNA vector between the translation start signal and the DNA sequence coding for the factor. A signal or signal-leader sequence is a sequence of amino acids at the amino terminus of a polypeptide or protein which provides for secretion of the protein or polypeptide from the cell in which it is produced. Many such signal and signal-leader sequences are known.

By including a DNA sequence encoding a signal or signal-leader amino acid sequence in the vectors of the invention, the factor may be secreted from the cell in which it is produced. Preferably, the signal or signal-leader amino acid sequence is cleaved from the factor during its secretion from the cell. If not, the factor should preferably be cleaved from the signal or signal-leader amino acid sequence after isolation of the factor.

Signal or signal-leader sequences suitable for use in the invention include *Saccharomyces cerevisiae* alpha factor (see U.S. Pat. No. 4,546,082), *S. cerevisiae* a factor (see U.S. Pat. No. 4,588,684), and signal sequences which are normally part of precursors of proteins or polypeptides such as the precursor of interferon (see U.S. Pat. No. 4,775,622).

The resulting vector is used to transform an appropriate host. This transformation may be performed using methods well-known in the art.

Any of a large number of available and well-known host cells may be used in the practice of this invention. The selection of a particular host is dependent upon a number of factors recognized by the art. These include, for example, compatibility with the chosen expression vector, toxicity to it of the factor, rate of transformation, ease of recovery of the factor, expression characteristics, bio-safety and costs. A balance of these considerations must be struck with the understanding that not all hosts may be equally effective.

Within these general guidelines, useful hosts include bacteria (such as *E. coli* sp.), yeast (such as *Saccharomyces* sp.) and other fungi, insects, plants, mammalian (including human) cells in culture, or other hosts known in the art.

Next, the transformed host is cultured under conventional fermentation conditions so that the factor is expressed. Such culture conditions are well-known in the art.

EXAMPLES

EXAMPLE 1: Preparation Of Lactoferrin-Induced Factor

A. Injection of Mice

Female $C_3H/HeJ$ mice (endotoxin resistant), 8 to 12 weeks old were purchased from Jackson Laboratories, Bar Harbor, Me. They were housed in a laminar flow animal station (Germfree Laboratories, Miami, Fla.) and were permitted continuous access to food and water.

The mice were injected intravenously with either: 1) control diluent consisting of pyrogen-free PBS (0.01M sodium phosphate and 0.15M NaCl, pH 7.4); or 2) 100 ug per mouse of iron-saturated human LF (FeLF) dissolved in pyrogen-free PBS. Age-matched mice were used for control and treated groups.

The FeLF was prepared by dissolving LF isolated from human breast milk (>90% pure, purchased from Sigma Chemical Co., St. Louis, Mo., catalog no. L8010) in PBS at 10 mg/ml. Then a solution of ascorbic acid and ferric ammonium sulfate was added to yield a final concentration 8 mg/ml LF, 0.8 mM ascorbic acid and 0.26 mM ferric ammonium sulfate. This mixture was rotated at room temperature for 2 hours, then dialysed against 3 liters of PBS (1 liter at a time for 8 hours, with 2 changes of PBS) at 4° C. in 3000-5000 molecular weight cut-off dialysis tubing (Spectrum Medical Industries, Los Angeles, Calif.). The resulting FeLF was filter sterilized (0.22 u filter) and stored at 4° C. until used. However, FeLF should be stored at most a few weeks.

Before use, the FeLF was depleted of endotoxin by passing it through a 1.0×3.0 cm column of Detoxigel (Pierce, Rockford, Ill.) that had been equilibrated with sterile PBS. Detoxigel is a resin that specifically binds endotoxin, and it is important to remove endotoxin because it is known to stimulate macrophages to produce monokines. The FeLF was eluted from the Detoxigel column with PBS, and the endotoxin concentration of the eluate was determined using the Limulus amoebocyte lysate agglutination assay (Sigma Chemical Co., St. Louis, Mo.). FeLF prepared as described contained less than 0.5 ng/ml endotoxin, which is the limit of detectability for the assay. Furthermore, $C_3H/HeJ$ mice which are endotoxin resistant were used to insure that any small amount of undetectable endotoxin present in the FeLF preparation would not be the reason for the production of the inhibitory activity.

The protein concentration of the eluate from the Detoxigel column was determined using a Bio-Rad colorimetric protein assay (Bio-Rad, Richmond, Calif.).

B. Preparation of Conditioned Medium

The mice injected as described in Part A were sacrificed by cervical dislocation 6 hours after injection, and the femurs and spleens were removed under sterile conditions. Spleen cells were prepared by pressing the spleens between the frosted ends of two sterile microscope slides. Bone marrow (BM) cells were obtained by flushing each femur with cold McCoy's 5A medium. Single-cell suspensions of BM and spleen were prepared by gentle refluxing through a Pasteur pipette. All cell suspensions were washed twice in McCoy's 5A medium supplemented with 10% fetal calf serum (HyClone Sterile Systems, Logan, Utah), penicillin and streptomycin and kept at 4° C. until used.

BM cells were incubated at a concentration of $1 \times 10^6$ cells/ml and spleen cells were incubated at a concentration of $10 \times 10^6$ cells/ml in supplemented McCoy's 5A medium in the presence of $10^{-6}M$ indomethacin, which is used to inhibit $PGE_2$ production. BM and spleen cells from control and FeLF-treated mice were allowed to condition the medium for 24 and 48 hours in 75 sq. cm. tissue culture flasks at 37° C., then filtered (Acrodisc disposable filter assembly, Gelman Sciences, Ann Arbor, Mich.) to produce a sterile, cell-free supernatant (CM). Each CM was tested at 10% v/v in the CFU-GM assay described below in Part C. Each batch of CM was also tested for the presence of endotoxin by using the Limulus lysate assay. This assay, which has a sensitivity range to 0.5 ng/ml, detected no endotoxin in any of the CM.

C. Assay for CFU-GM Colony and Cluster Formation

The CM's prepared in Part B were assayed for the ability to inhibit CFU-GM colony and cluster formation. To perform this assay, a single-cell suspension of BM cells from normal, untreated female C3H/HeJ mice was prepared as described above in part A. The BM cells were cultured in Petri dishes in a soft agar medium containing 0.3% Bactoagar (Difco) in McCoy's 5A medium containing 10% fetal calf serum (HyClone Sterile Systems, Logan, Utah), penicillin and streptomycin. The concentration of BM cells utilized in the CFU-GM assay was $1 \times 10^5$ cells/ml.

Proliferation of CFU-GM was stimulated by the addition to each culture of 0.1 ml (10% v/v) of CSF-GM obtained from CBA/J spleen cells stimulated by 5% pokeweed mitogen (PWMSCM) which was prepared as described in Metcalf and Johnson, *J. Cell. Physiol.*, 96, 31 (1978). The PWMSCM stimulates 64% monocytoid, 11% mixed monocytoid-neutrophil, 24% neutrophil and <1% eosinophil colony and cluster formation.

In addition, each culture contained either 0.1 ml of McCoy's 5A medium (Control), 0.1 ml of CM prepared from control mice, or 0.1 ml CM prepared from FeLF-treated mice. The total volume of each culture was 1 ml.

The cultures were incubated in a fully humidified 5% $CO_2$ atmosphere. Triplicate cultures were established for each control or CM preparation. Total colonies (>50 cells) and clusters (4 to 50 cells) were scored after 5 days.

The results of the assays are given below in Table 1 and 2. The results show that CM produced by culturing BM or spleen cells from mice injected with FeLF significantly inhibited CFU-GM colony and cluster formation.

TABLE 1

Effect of BM CM on CFU-GM Colony And Cluster Formation

| Material | Colonies (mean ± s.e.) | % Change | Colonies + Clusters (mean ± s.e.) | % Change |
|---|---|---|---|---|
| Control | 90 ± 2 | — | 180 ± 4 | — |
| Control CM (24 hr.) | 104 ± 7# | +16 | 193 ± 9# | +6 |
| LF CM (24 hr.) | 72 ± 3* | −20 | 112 ± 5* | −38 |
| Control CM (48 hr.) | 102 ± 6# | +13 | 191 ± 6# | +6 |
| LF CM (48 hr.) | 59 ± 5* | −34 | 106 ± 4* | −41 |

Not statistically significant as compared to Control by the student's t test.
*Significantly different compared to Control ($p < 0.0005$) by the student's t test.

TABLE 2

Effect of Spleen CM on CFU-GM Colony And Cluster Formation

| Material | Colonies (mean ± s.e.) | % Change | Colonies + Clusters (mean ± s.e.) | % Change |
|---|---|---|---|---|
| Control | 90 ± 2 | — | 180 ± 4 | — |
| Control CM (24 hr.) | 101 ± 9# | +12 | 190 ± 6# | +6 |
| LF CM (24 hr.) | 57 ± 4* | −37 | 103 ± 6* | −43 |
| Control CM (48 hr.) | 97 ± 6# | +8 | 181 ± 4# | 0 |
| LF CM (48 hr.) | 55 ± 6* | −39 | 101 ± 7* | −44 |

Not statistically significant as compared to Control by student's t test.
*Significantly different compared to control ($p < 0.0005$) by student's t test.

EXAMPLE 2: Preparation of Lactoferrin-Induced Factor

Example 1 was repeated using BM cells, but no fetal calf serum was used in the medium during preparation of the CM. Also, the medium was conditioned for 24 hours only.

The results of the assay for inhibition of CFU-GM colony and colony plus cluster formation are shown in Table 3. As can be seen, comparable inhibition was obtained without the use of serum as was obtained with it. Accordingly, CM prepared without the use of serum was used for further purification of the inhibitory activity.

TABLE 3

Effect of BM CM on CFU-GM Colony And Cluster Formation

| Material | Colonies (mean ± s.e.) | % Change | Colonies + Clusters (mean ± s.e.) | % Change |
|---|---|---|---|---|
| Control | 77 ± 5 | — | 167 ± 7 | — |
| Control CM | 84 ± 2# | +9 | 166 ± 4# | −1 |
| LF CM | 38 ± 1* | −51 | 74 ± 2* | −56 |

Not statistically significant compared to Control by student's t test.
*Significantly different compared to control ($p < 0.0005$) by student's t test.

EXAMPLE 3: Purification of The Inhibitory Activity

A. Concentration Of The Inhibitory Activity

Bm Cm prepared as described Example 2 was brought to 80% ammonium sulfate by directly adding ammonium sulfate (561 g/l) to the CM with gentle stirring at 4° C. Stirring was continued at 4° C. for one hour after the ammonium sulfate had dissolved. The resulting precipitate was collected by centrifugation at $10,000 \times g$ for 30 minutes in a Beckman refrigerated centrifuge at 4° C. The preciptate was then dissolved in 0.01M sodium phosphate, pH 7.4, and the solution was centrifuged at $10,000 \times g$ as before to remove any remaining particulates. The supernatant containing the inhibitory activity was filter sterilized (0.22 u filter) and stored at 4° C. until used.

The dissolved precipitate was next filtered through a 10,000 molecular weight cut-off ultrafilter membrane (Omegacell-5, purchased from Pharmacia, Piscataway, N.J.) in a "stirred cell" ultrafilter (Pharmacia). The filtrate from this step was then concentrated on a 5,000 molecular weight cut-off Omegacell-5 ultrafilter membrane, and the retentate was further processed as described below. Crude CM ammonium sulfate precipitate was routinely concentrated about 20 fold by the ultrafiltration.

B. Gel Filtration

The retentate from the ultrafiltration in 0.01M sodium phosphate, pH 7.4, was passed through a 1.6×30 cm column of Sephadex G-25 Superfine (Pharmacia) that had been pressure packed at 3.0 column volumes per hour. Sample size loaded was 4-5 ml. The column was eluted with 0.01M sodium phosphate, pH 7.4, at 2.0 ml/minute, and 1 ml fractions were collected.

Elution of the column was monitored by continuously measuring $OD_{280}$. Also, each of the collected fractions was tested for its ability to inhibit CFU-GM colony and cluster formation as described in Part C of Example 1. The optical density measurements and the CFU-GM assay results are presented in FIG. 1. Active fractions were pooled, filter sterilized and stored at 4° C. until used.

C. Anion Exchange Chromatography

The pool of active fractions obtained after gel filtration was concentrated 10-20 fold on a 5,000 molecular weight cut-off ultrafilter membrane as described in Part A of this Example, and the retentate was applied to a Mono-Q high-resolution anion exchange column (Pharmacia). The column, 0.5×5.0 cm, had previously been equilibrated with 0.01M sodium phosphate, pH 7.4. The column was loaded at 1.0 ml/minute, and it was washed with 5 column volumes to collect the sample effluent (unbound fraction). This was collected in 1 ml fractions. Then the column was eluted with a linear gradient of NaCl in 0.01M sodium phosphate, pH 7.4, from 0 to 1.0M over 15 column volumes, and 1 ml fractions were collected.

Figure 2:
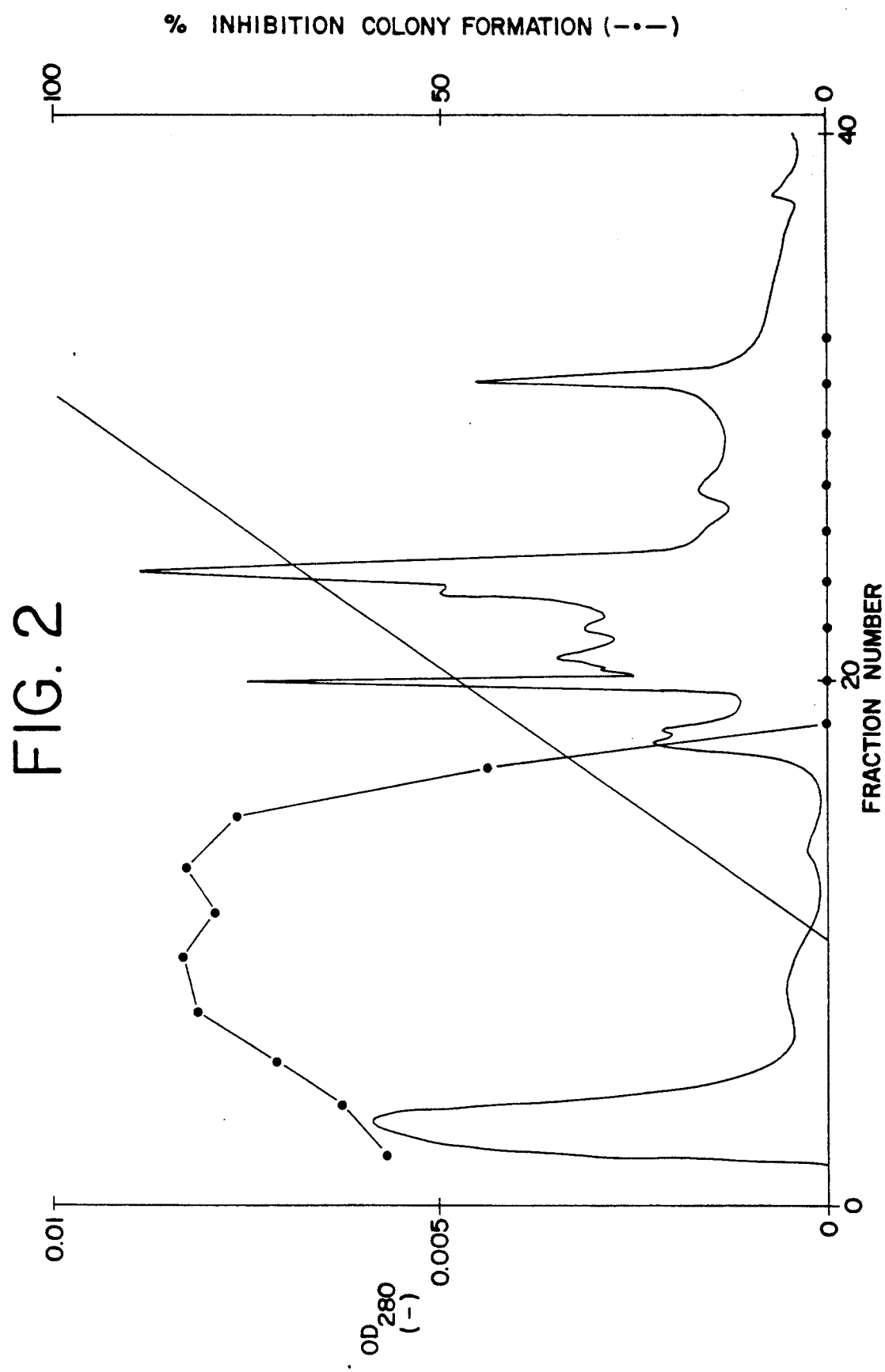
FIG. 2 shows the elution pattern obtained by passing the pooled active fractions from the Sephadex G25 Superfine column of FIG. 1 over a Mono Q column at pH 7.4.

Elution of the column was monitored by continuously measuring $OD_{280}$. Also, each of the collected fractions was tested for its ability to inhibit CFU-GM colony and cluster formation as described in Part C of Example 1. The optical density measurements and the CFU-GM assay results are presented in FIG. 2. As can be seen in FIG. 2, the inhibitory activity was only slightly retarded on the Mono Q column, indicating that it has a weak anionic charge at pH 7.4. Active fractions were pooled, filter sterilized and stored at 4° C. until used.

D. SDS-PAGE

The pool of active fractions obtained after anion exchange chromatography was concentrated 10-20 fold on a 5,000 molecular weight cut-off ultrafilter membrane as described in Part A of this Example, and the retentate was subjected to SDS-PAGE. SDS-PAGE was performed according to the method of Laemmli (Laemmli, *Nature*, 277, 680-85 (1970)) in a 4% stacking gel and 12% separating gel. Samples were not reduced before application to the gel. The gel was run in a Bio-Rad Protein-II electrophoresis system (Bio-Rad, catalog no 165-1801) at 20 milliamps constant current for about 4 hours until the marker dye was at the bottom of the gel.

Two gels were run. After electrophoresis, one gel was stained with the Bio-Rad Silver Stain Kit to detect proteins. The lanes of the other gel were sliced into 1.0 cm slices, and each slice was eluted into PBS with agitation overnight at 4° C. (1.0 ml/slice). These eluates were assayed for inhibitory activity in the CFU-GM assay described in Part C of Example 1. Location of the inhibitory activity was compared with the location of the visualized protein bands.

Figure 3:
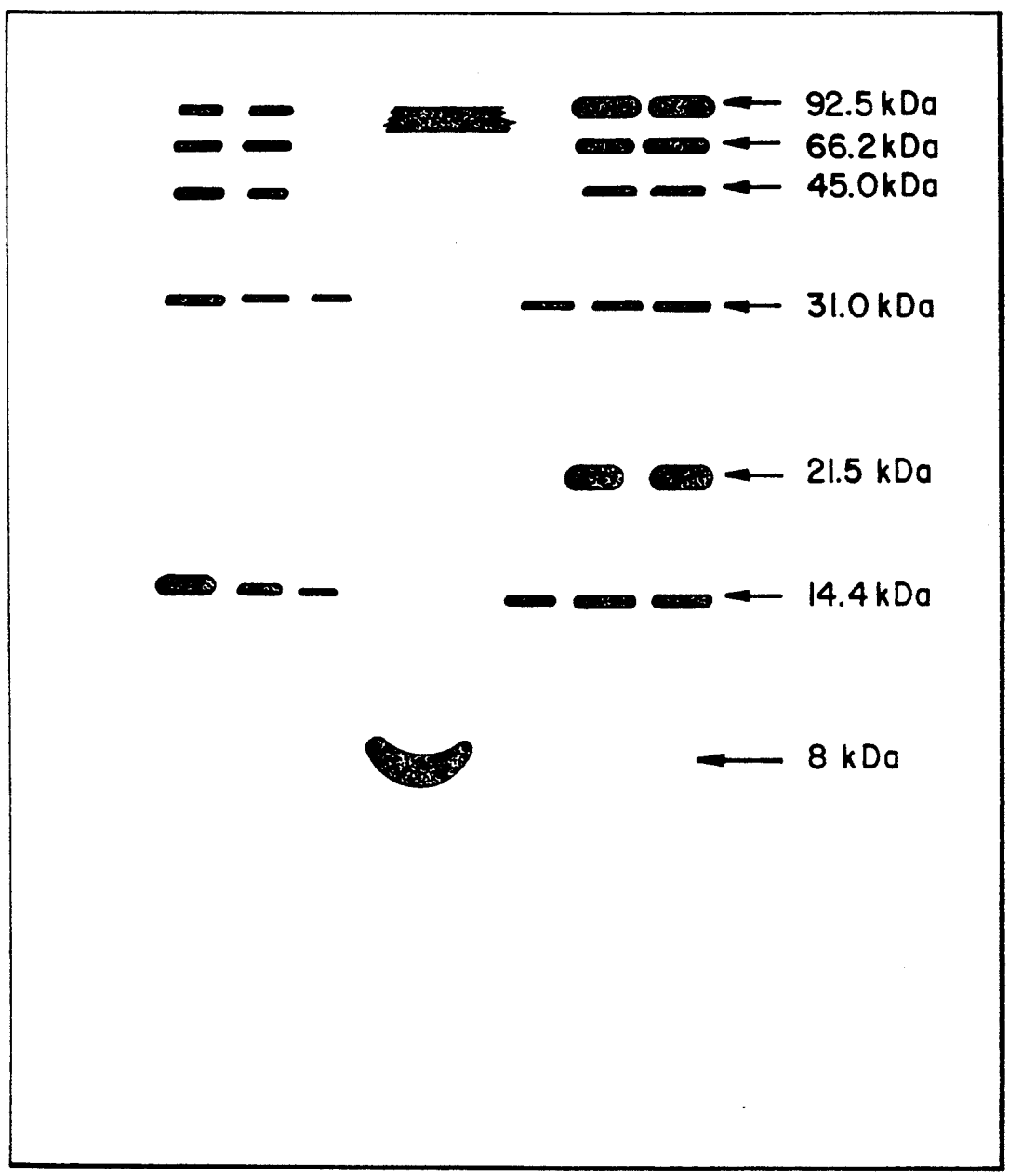
FIG. 3 shows a sketch of a silver-stained SDS-PAGE gel prepared by electrophoresing the pooled active fractions from the Mono Q column of FIG. 2.

A sketch of the silver-stained gel is shown in FIG. 3. As can be seen, the silver staining revealed only a single band in the lane in which the pool of active fractions from the Mono Q column was electrophoresed (middle lane). This band appeared to be homogenous.

Standards were also run on the gels. The standards used were: hen egg white lysozyme (14.4 kDa); soy bean trypsin inhibitor (21.5 kDa); bovine carbonic anhydrase (31.0 kDa); hen egg white ovalbumin (42.699 kDa); bovine serum albumin (66.2 kDa); and rabbit muscle phosphorylase (97.4 kDa). Using these standards, a molecular weight of approximately 8 kDa was calculated for the single band.

Figure 4:
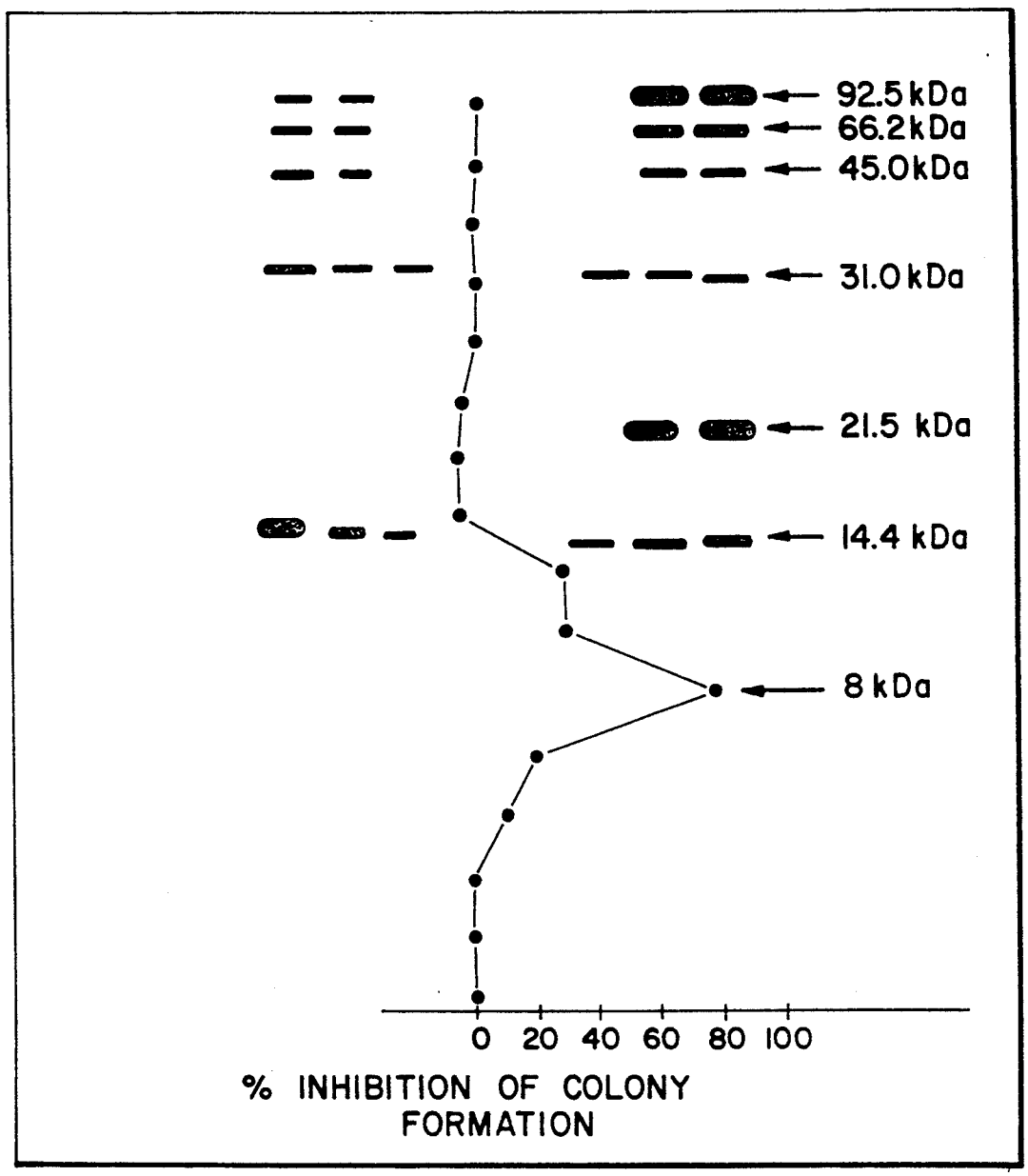
FIG. 4 shows a sketch of the same SDS-PAGE gel as shown in FIG. 3, but with the lane in which the factor of the invention was electrophoresed having been removed. A plot of inhibition of CFU-GM colony formation for eluates of the removed slices of the lane versus approximate position of the slice is shown.

The results of the CFU-GM assay are set forth in Table 4 and FIG. 4. These results show that the material eluted from the band (Eluates 9-13) inhibited CFU-GM colony and cluster formation. Inhibitory activity was not eluted from any other portion of the lane (see Table 4 and FIG. 4).

TABLE 4

Effect of SDS-PAGE Fractions on CFU-GM Colony And Cluster Formation

| Material | Colonies (mean ± s.e.) | % Change | Colonies + Clusters (mean ± s.e.) | % Change |
|---|---|---|---|---|
| Control Eluate | 103 ± 4 | — | 166 ± 1 | — |
| 1 | 101 ± 3 | −2 | 166 ± 2 | 0 |
| 2 | 99 ± 3 | −4 | 160 ± 4 | +4 |
| 3 | 104 ± 5 | 0 | 161 ± 4 | +3 |
| 4 | 101 ± 4 | −2 | 166 ± 4 | 0 |
| 5 | 101 ± 6 | −2 | 167 ± 6 | 0 |
| 6 | 111 ± 6 | +7 | 174 ± 7 | +5 |
| 7 | 101 ± 5 | +7 | 166 ± 6 | 0 |
| 8 | 107 ± 3 | +4 | 169 ± 4 | +2 |
| 9 | 72 ± 7 | −30 | 131 ± 13 | −21 |
| 10 | 71 ± 3 | −30 | 131 ± 2 | −21 |
| 11 | 30 ± 9 | −72 | 62 ± 11 | −63 |
| 12 | 79 ± 9 | −25 | 135 ± 17 | −19 |
| 13 | 87 ± 7 | −16 | 149 ± 10 | −10 |
| 14 | 101 ± 3 | −2 | 170 ± 5 | +2 |
| 15 | 103 ± 5 | 0 | 166 ± 4 | 0 |
| 16 | 101 ± 4 | −2 | 168 ± 4 | +1 |

EXAMPLE 4: Preparation of Acidic Isoferritin-Induced Factor

Example 1 was repeated using 100 ug of recombinant human H subunit acidic ferritin (rHF) instead of the 100 ug of FeLF. The rHF was prepared as described in Levi et al., *Gene*, 51, 267 (1987).

The results of the assay of the unpurified CM are shown in Table 5 and 6 below. As shown there, CM prepared by culturing BM or spleen cells from mice injected with rHF significantly inhibited CFU-GM colony and cluster formation.

TABLE 5

Effect of BM CM on CFU-GM Colony And Cluster Formation

| Material | Colonies (mean ± s.e.) | % Change | Colonies + Clusters (mean ± s.e.) | % Change |
|---|---|---|---|---|
| Control | 90 ± 2 | — | 180 ± 4 | — |
| Control CM (24 hr.) | 104 ± 7# | +16 | 193 ± 9# | +6 |
| rHF CM (24 hr.) | 55 ± 1* | −39 | 98 ± 5* | −46 |
| Control CM (48 hr.) | 102 ± 6# | +13 | 191 ± 6# | +6 |

TABLE 5-continued

Effect of BM CM on CFU-GM Colony And Cluster Formation

| Material | Colonies (mean ± s.e.) | % Change | Colonies + Clusters (mean ± s.e.) | % Change |
|---|---|---|---|---|
| rHF CM (48 hr.) | 54 ± 2* | −40 | 90 ± 3* | −50 |

Not statistically significant as compared to Control by student's t test.
*Statistically significant as compared to Control (p < 0.0005) by student's t test.

TABLE 6

Effect of Spleen CM on CFU-GM Colony And Cluster Formation

| Material | Colonies (mean ± s.e.) | % Change | Colonies + Clusters (mean ± s.e.) | % Change |
|---|---|---|---|---|
| Control | 90 ± 2 | — | 180 ± 4 | — |
| Control CM (24 hr.) | 101 ± 9# | +12 | 190 ± 6# | +6 |
| rHF CM (24 hr.) | 55 ± 2* | −39 | 101 ± 4* | −44 |
| Control CM (48 hr.) | 97 ± 6# | +8 | 181 ± 4# | 0 |
| rHF CM (48 hr.) | 54 ± 4* | −40 | 88 ± 3* | −51 |

Not statistically significant compared to Control by student's t test.
*Statistically significant as compared to Control (p < 0.0005) by student's t test.

EXAMPLE 5: Purification of Acidic Isoferritin-Induced Factor

BM CM was prepared as described in Example 4, except that no fetal calf serum was used in the medium during preparation of the CM. Also, the medium was conditioned for 24 hours only.

This BM CM was purified as described in Example 3, except that another standard was used on the SDS-PAGE gel. That standard was insulin, 6 kDa.

Figure 5:
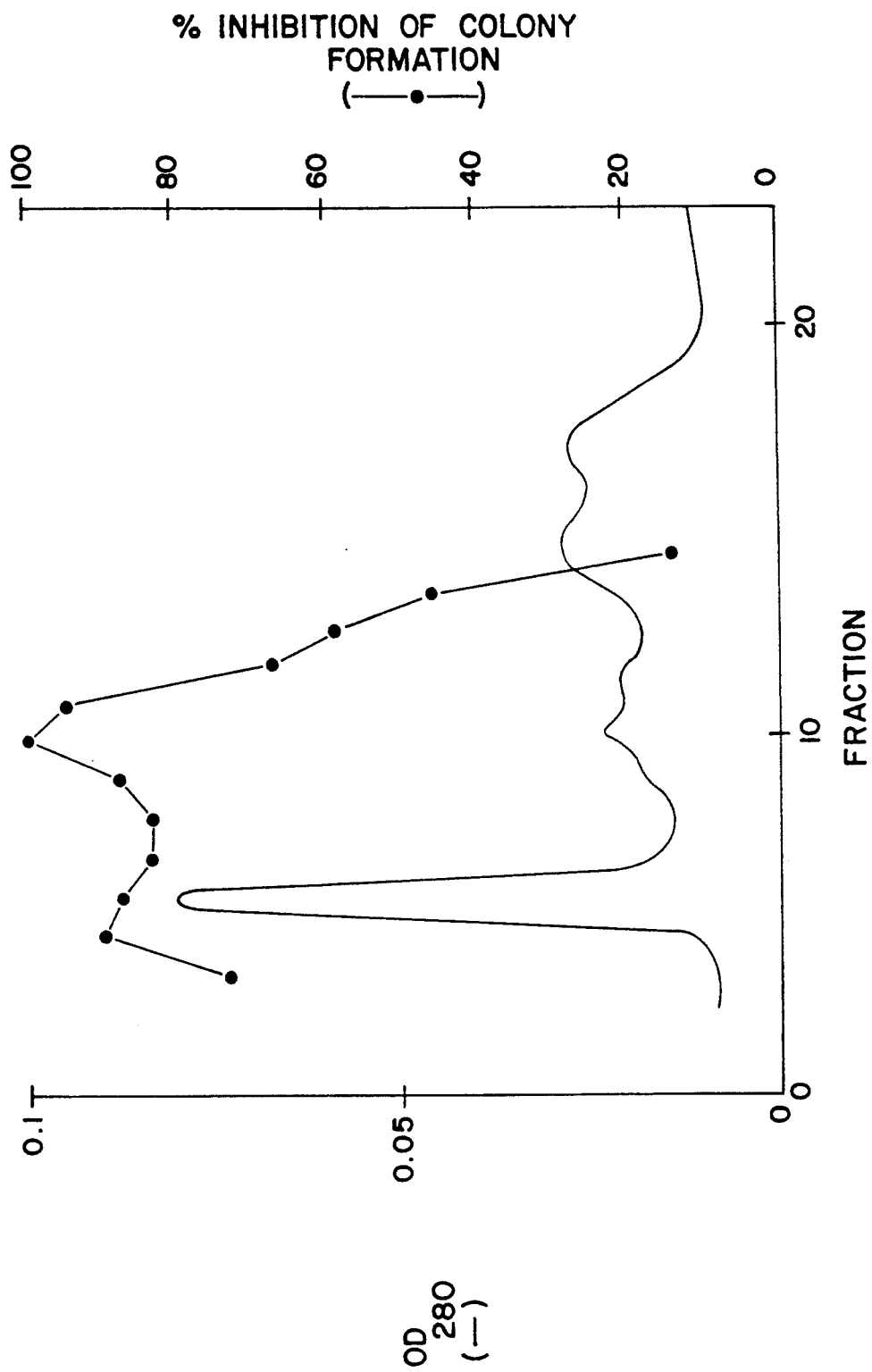
FIG. 5 shows the elution pattern from a Sephadex G25 Superfine column of concentrated CM prepared by culturing BM cells from mice injected with rHF.
Figure 6:
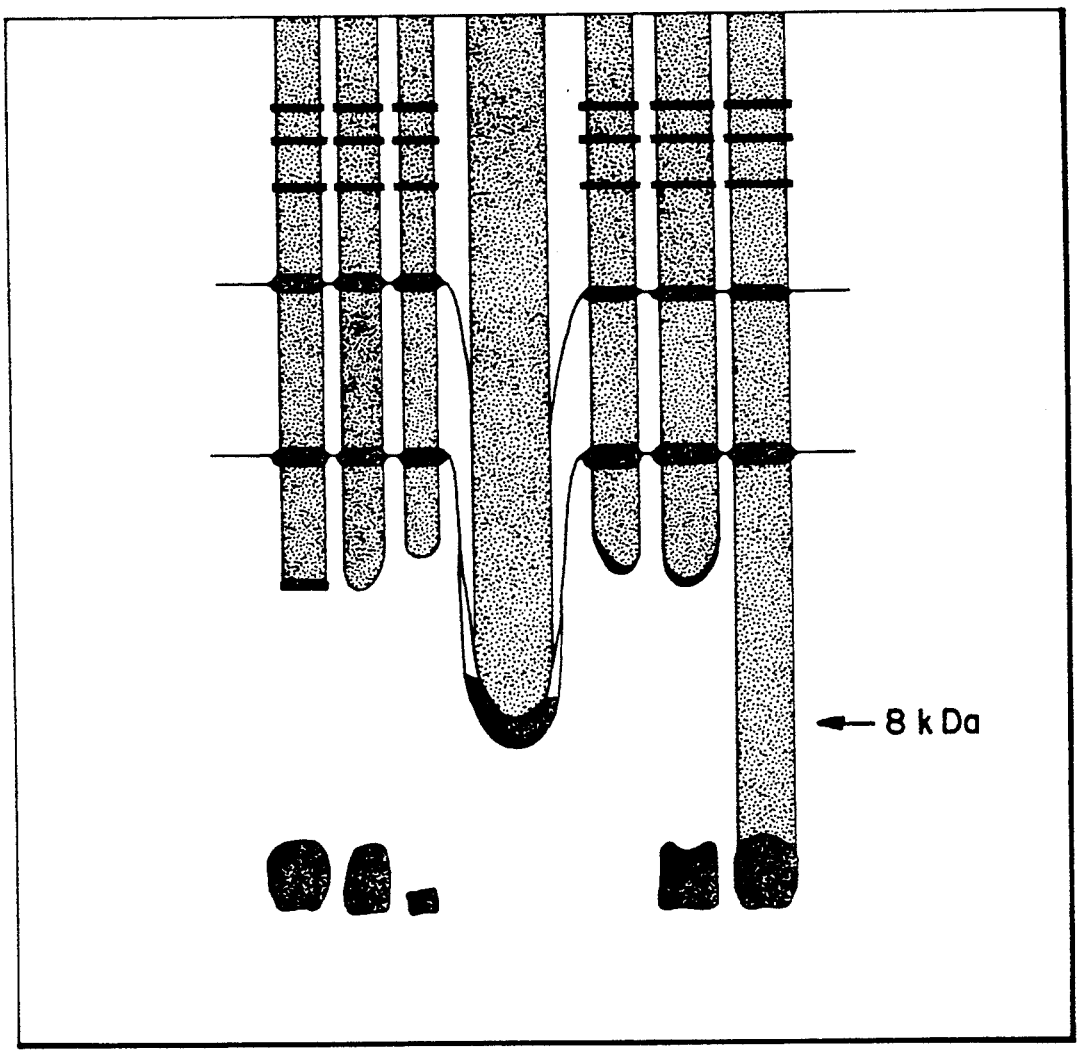
FIG. 6 shows a sketch of a silver-stained SDS-PAGE gel.

Similar results were obtained as for the purification of the LF-induced factor. See FIG. 5 which shows the elution profile from Sephadex G25 Superfine and FIG. 6 which shows a sketch of the silver-stained SDS-PAGE gel.

Inhibitory activity of the fractions from the Mono Q column was not evaluated, but fractions believed to have inhibitory activity (as based on the results with the LF-induced factor) were pooled, concentrated and subjected to SDS-PAGE.

The silver staining on the SDS-PAGE gel was quite dark, but a band could be detected between the 6 kDa and 14 kDa markers in the middle lane in which the pooled fractions from the Mono Q column were electrophoresed. This band appeared to be homogenous and to have a molecular weight of approximately 8 kDa.

EXAMPLE 7: Isoelectric Behavior of the Factor

BM CM prepared as described in Example 2 was concentrated with ammonium sulfate as described in Example 3. The dissolved precipitate was passed through a column of Sephadex G-25 Superfine as described in Example 3, except that the Sephadex G-25 Superfine column was eluted with 0.01M Tris-HCl, pH 9.0. The pool of active fractions was concentration on a 5,000 molecular weight cutoff ultrafilter, and the retentate was applied to a Mono-Q high-resolution anion exchange column, all as described in Example 3, except that the Mono Q column was run using 0.01M Tris-HCl, pH 9.0, instead of 0.01M sodium phosphate, pH 7.4.

Figure 7:
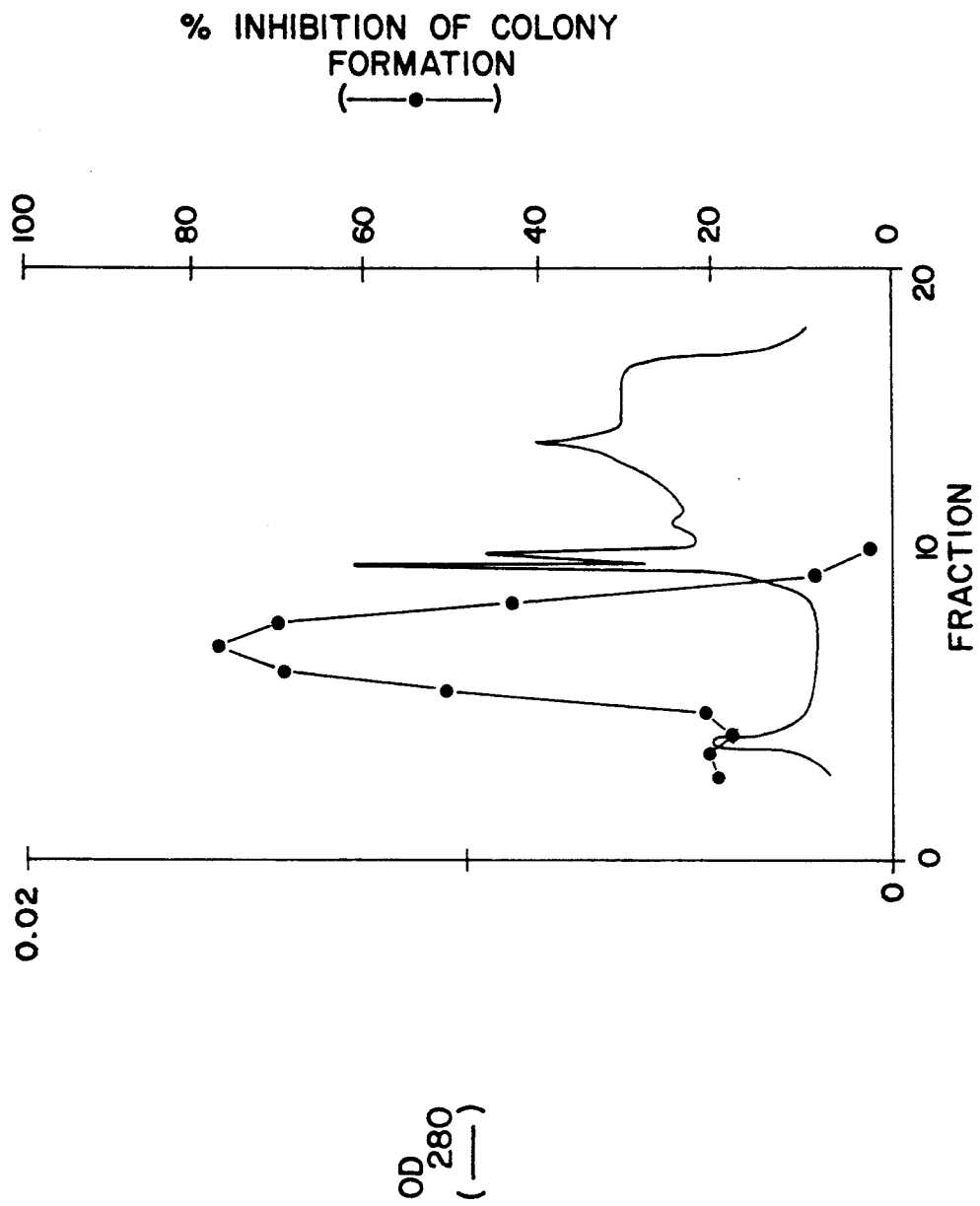
FIG. 7 shows the elution pattern obtained by passing the pooled active fractions from the Sephadex G25 Superfine column of FIG. 1 over a Mono Q column at pH 9.0.

The results are shown in FIG. 7. As can be seen, the elution pattern at pH 9.0 is essentially the same as the elution pattern at pH 7.4, except that the inhibitor activity was eluted from the column slightly sooner at pH 9.0 (compare FIG. 2 and 7). This result coupled with the results of the Mono Q run in Example 3 indicates that the isoelectric titration curve of the factor is flattened around the pI.

We claim:

1. A method of making a biologically active protein factor comprising:

injecting a mouse with iron-saturated, endotoxin-depleted lactoferrin or with acidic isoferritin; and conditioning a culture medium from a sufficient time with bone marrow or spleen cells removed from the mouse a sufficient time after the injection of the mouse with lactoferrin or acidic isoferritin to effect production of the factor; and purifying the factor which:

a) inhibits granulocyte-macrophage colony and cluster formation;

b) has a molecular weight of about 8 kDa as determined by SDS-PAGE;

c) has a weak anionic charge at pH 7.4 as shown by anion exchange chromatography; and d) has a flattened isoelectric titration curve as shown by anion exchange chromatography.

2. The method of claim 1 wherein the acidic isoferritin is recombinant human H subunit acidic ferritin.

3. The method of claim 1 wherein the mouse is a $C_3H/HeJ$ mouse.

4. The method of claim 1 wherein the factor is purified by:

subjecting the factor to size-exclusion chromatography;

subjecting the factor to anion exchange chromatography; and then subjecting the factor to SDS-PAGE.

5. A method of making a conditioned medium containing a biologically active protein factor, the method comprising:

injecting a mouse with iron-saturated, endotoxin-depleted lactoferrin or with acidic isoferritin; and conditioning a culture medium for a sufficient time with bone marrow or spleen cells removed from the mouse a sufficient time after the injection of the mouse with lactoferrin or acidic isoferritin to effect production of the factor which a) inhibits granulocyte-macrophage colony and cluster formation;

b) has a molecular weight of about 8 kDa as determined by SDS-PAGE;

c) has a weak anionic charge at pH 7.4 as shown by anion exchange chromatography; and d) has a flattened isoelectric titration curve as shown by anion exchange chromatography.

6. The conditioned medium produced by the method of claim 5.

* * * * *

UNITED STATES PATENT AND TRADEMARK OFFICE
CERTIFICATE OF CORRECTION

PATENT NO. : 5,294,544
DATED : March 15, 1994
INVENTOR(S) : Patrick S. Gentile et al It is certified that error appears in the above-indentified patent and that said Letters Patent is hereby corrected as shown below:

IN THE REFERENCES CITED

On the title page, under "OTHER PUBLICATIONS", column 2, line 7, delete "Genitle" and substitute therefor --Gentile--.

On the title page, under "OTHER PUBLICATIONS", column 2, line 8, delete "Genitle" and substitute therefor --Gentile--.

In column 1, line 41, after "also", delete "." and substitute therefor --,--.

In column 2, line 21, after "CFU-GM", insert --.--.

In column 3, line 23, delete "lipopolysaccharide".

In column 3, line 24, delete "phytohemagglutinin".

In column 3, line 58, after "SDS-PAGE", insert --.--.

In column 5, line 27, after "purified", insert --.--.

UNITED STATES PATENT AND TRADEMARK OFFICE
CERTIFICATE OF CORRECTION

PATENT NO. : 5,294,544
DATED : March 15, 1994
INVENTOR(S) : Patrick S. Gentile et al It is certified that error appears in the above-indentified patent and that said Letters Patent is hereby corrected as shown below:

In column 10, line 47, delete "Bm Cm" and substitute therefor --BM CM--.

In column 10, line 54, delete "preciptate" and substitute therefor --precipitate--".

In column 11, line 55, after "Nature,", delete "277" and substitute therefor --227--.

In column 12, line 35, under "Colonies" and after "Control Eluate 7", delete "101" and substitute therefor --110--.

Column 14, claim 1, line 5, delete "from" and substitute therefor --for--.

Signed and Sealed this

Twenty-sixth Day of December, 1995

Attest:

BRUCE LEHMAN

*Attesting Officer*  *Commissioner of Patents and Trademarks*